(12) United States Patent
Rinear (10) Patent No.: US 12,128,205 B1
(45) Date of Patent: Oct. 29, 2024

(54) HUB ASSEMBLY WITH A SELF-CLOSING VALVE FOR USE WITH A SYRINGE

(71) Applicant: Daniel Rinear, Fisherville, KY (US)

(72) Inventor: Daniel Rinear, Fisherville, KY (US)

( * ) Notice: Subject to any disclaimer, the term of this patent is extended or adjusted under 35 U.S.C. 154(b) by 487 days.

(21) Appl. No.: 17/367,393

(22) Filed: Jul. 4, 2021

Related U.S. Application Data (60) Provisional application No. 63/049,529, filed on Jul. 8, 2020.

(51) Int. Cl.
*A61M 39/10* (2006.01)
*A61M 25/00* (2006.01)
*A61M 39/26* (2006.01)
*A61M 39/24* (2006.01)

(52) U.S. Cl.
CPC ........ *A61M 39/10* (2013.01); *A61M 25/0097* (2013.01); *A61M 39/26* (2013.01); *A61M 2039/2426* (2013.01); *A61M 2039/2473* (2013.01)

(58) Field of Classification Search
CPC ........ A61M 5/3293; A61M 2005/3128; A61M 25/0097; A61M 2025/0076; A61M 2025/0078; A61M 2039/0666; A61M 2039/2406; A61M 2039/242; A61M 2039/244; A61M 2039/246
See application file for complete search history.

(56) References Cited

U.S. PATENT DOCUMENTS

| | | | |
|---|---|---|---|
| 4,143,853 A | 3/1979 | Abramson | |
| 4,160,383 A * | 7/1979 | Rauschenberger | ... A61M 39/22 604/323 |
| 4,424,833 A | 1/1984 | Spector et al. | |
| 4,430,081 A * | 2/1984 | Timmermans | .... A61M 39/0606 251/149.1 |
| 4,449,693 A | 5/1984 | Gereg | |
| 4,765,588 A | 8/1988 | Atkinson | |
| 4,842,591 A | 6/1989 | Luther | |
| 4,935,010 A | 6/1990 | Cox et al. | |
| 5,180,365 A * | 1/1993 | Ensminger | ........ A61M 39/0208 604/288.03 |
| 5,224,938 A * | 7/1993 | Fenton, Jr. | ........ A61M 25/0075 604/9 |
| 5,295,969 A * | 3/1994 | Fischell | ............ A61M 39/0606 604/168.01 |
| 5,336,192 A | 8/1994 | Palestrant | |
| 5,405,323 A | 4/1995 | Rogers et al. | |
| 5,613,663 A * | 3/1997 | Schmidt | ................ A61M 39/26 604/167.03 |
| 5,858,007 A * | 1/1999 | Fagan | ................ A61B 17/3462 604/167.03 |
| 6,066,117 A * | 5/2000 | Fox | .................... A61B 17/3462 604/167.03 |

(Continued)

Primary Examiner — Kami A Bosworth
(74) Attorney, Agent, or Firm — Law Office of J. L. Simunic; Joan Simunic (57) ABSTRACT

The present development is a connection hub assembly for use with a syringe barrel or an IV line. The connection hub assembly includes a connection hub and a self-sealing valve that prevents blood, fluid or air, from flowing out of the connection hub assembly as the syringe barrel is removed. A retaining ring adapted to complement the self-sealing valve holds the valve in position in the connection hub. The connection hub is further attached to a needle, or maintained in a catheter, cannula or lumen.

12 Claims, 6 Drawing Sheets

(56) References Cited

U.S. PATENT DOCUMENTS

| | | | |
|---|---|---|---|
| 6,533,759 B1 | 3/2003 | Watson et al. | |
| 6,783,522 B2 | 8/2004 | Fischell | |
| 7,331,949 B2 | 2/2008 | Marisi | |
| 8,475,434 B2 | 7/2013 | Frojd | |
| 8,926,564 B2 * | 1/2015 | King | A61M 25/0668 604/167.03 |
| 9,408,971 B2 | 8/2016 | Carlyon | |
| 10,596,351 B2 | 3/2020 | Liska | |
| 2002/0045863 A1 * | 4/2002 | Wechler | A61M 39/24 604/167.03 |
| 2009/0247986 A1 * | 10/2009 | Rioux | A61M 39/24 604/247 |
| 2015/0306349 A1 * | 10/2015 | Bonnal | A61M 25/0097 604/272 |
| 2019/0298911 A1 | 10/2019 | Harward et al. | |
| 2020/0188634 A1 * | 6/2020 | Woehr | A61M 25/0097 |

\* cited by examiner

HUB ASSEMBLY WITH A SELF-CLOSING VALVE FOR USE WITH A SYRINGE

CROSS-REFERENCE TO PRIOR APPLICATIONS

The present application claims priority to U.S. Patent Application No. 63/049,529 filed 8 Jul. 2020, which is incorporated herein in its entirety by reference.

GOVERNMENT SUPPORT

The present application was developed without any government support.

FIELD OF THE INVENTION

The present invention relates to a hub assembly comprising a connection hub with a self-closing valve. The connection hub may also be attached to a needle or to a catheter. The self-closing valve precludes blood leakage as a syringe barrel is removed from the connection hub and replaced with a second syringe barrel or as an IV unit is coupled to the catheter.

BACKGROUND OF THE INVENTION

Venipuncture is defined as the puncture of a vein as part of a medical procedure, typically to withdraw a blood sample or for an intravenous injection. Venipuncture may be performed with a needle attached to a syringe or with an over the needle catheter. Intravenous (IV) procedures are commonly used in the medical arts to deliver medications and other fluids to patients.

As is known in the art, a syringe normally comprises a barrel with an end adapted to connect to a needle hub or a connection hub. During a medical procedure, a needle may be attached to a first syringe, the needle is inserted into a patient's vein, and medication within the syringe barrel is injected into the patient. If multiple medications need to be administered, rather than removing the needle the practitioner normally disconnects the first syringe at the connection hub and connects a second syringe to the same connection hub. However, when the first syringe is removed, blood can easily backflow from the punctured vessel through the needle and connection hub, obscuring the work area and putting the practitioner at risk of exposure to blood-borne pathogens.

Typically, an IV procedure is initiated by having a needle encircled by a catheter or plastic sleeve pierce a patient's skin. The needle and catheter are then inserted into a vein or artery to provide the practitioner with access to the circulatory system. The needle is then removed from the catheter, and an IV line is attached to a connection hub. When the needle, which is commonly attached to a syringe, is within the catheter a positive pressure is applied against the blood coursing through the punctured vein or artery so that blood remains in the blood vessel. However, once the needle is removed from the catheter and before the IV line is attached to the connection hub blood can freely flow from the punctured vessel through the catheter. The blood exiting the catheter obscures the working area and exposes the practitioner to direct contact with the patient's blood.

Because intravenous procedures are so common and important in the medical arts, it would be advantageous to have a connection hub designed to keep the blood from exiting through the needle or catheter when the syringe is removed and before the replacement syringe or the IV line is attached. Preferably the design should be relatively simple, thereby reducing the possibility of a failure of the system, and should be capable of being used with the current syringe barrels and IV lines without the need for adapters.

SUMMARY OF THE PRESENT INVENTION

The present development is a connection hub assembly comprising a connection hub with a self-closing valve for use with a syringe barrel. The connection hub is further attached to a needle or catheter, and is adapted to receive a syringe barrel or an IV line. The connection hub assembly includes a self-sealing valve that prevents blood from flowing out of the connection hub assembly as the syringe barrel is removed.

DETAILED DESCRIPTION OF THE PRESENT DEVELOPMENT

The hub assembly depicted in the various Figures is selected solely for the purposes of illustrating the invention. Other and different hub assemblies may utilize the inventive features described herein as well.

Reference is first made to FIGS. 1 through 6 in which the hub assembly constructed in accordance with the present invention is generally noted by the character numeral 10. The hub assembly 10 has as major components a connection hub 20, a self-closing valve 30, and a retaining ring 36. Optionally, a device that can be inserted into a vein or artery 40, including but not limited to a needle or a catheter (not shown) or a cannula, may be attached to the connection hub 20. The device that can be inserted into a vein or artery 40 will be referred to as a "catheter" herein, but the term is intended to encompass any variation of device 40.

Figure 1:
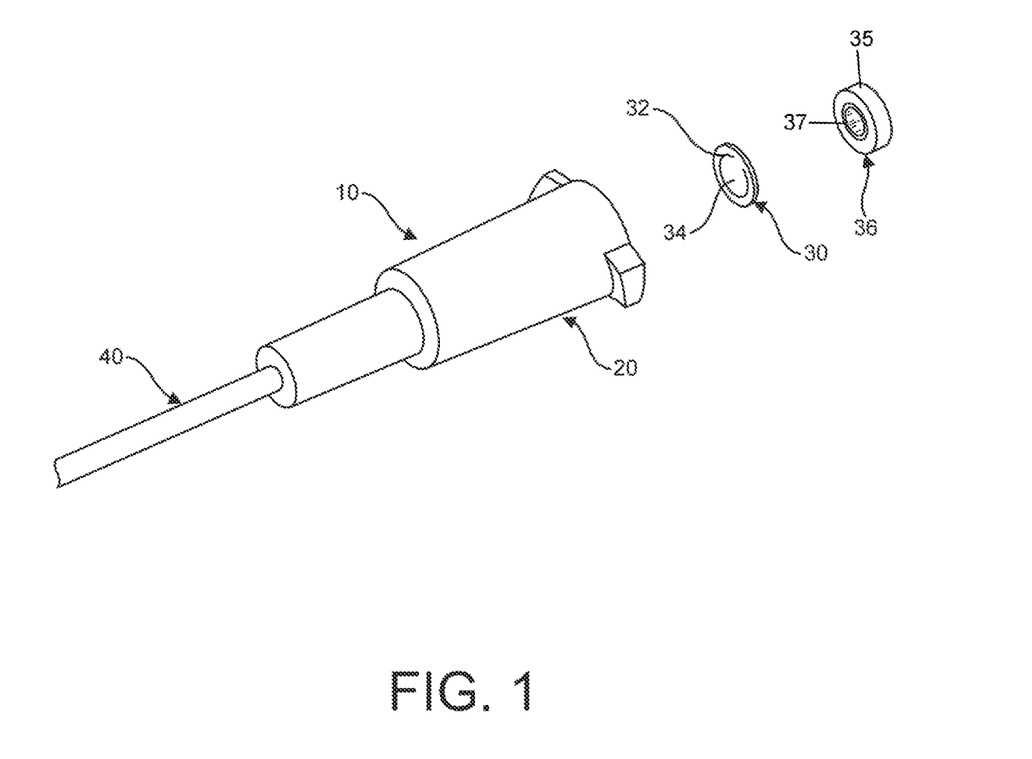
FIG. 1 is a perspective view of a connection hub made in accordance with the present invention showing a self-closing valve and retaining ring before insertion into the connection hub and showing a catheter attached to the connection hub.
Figure 2:
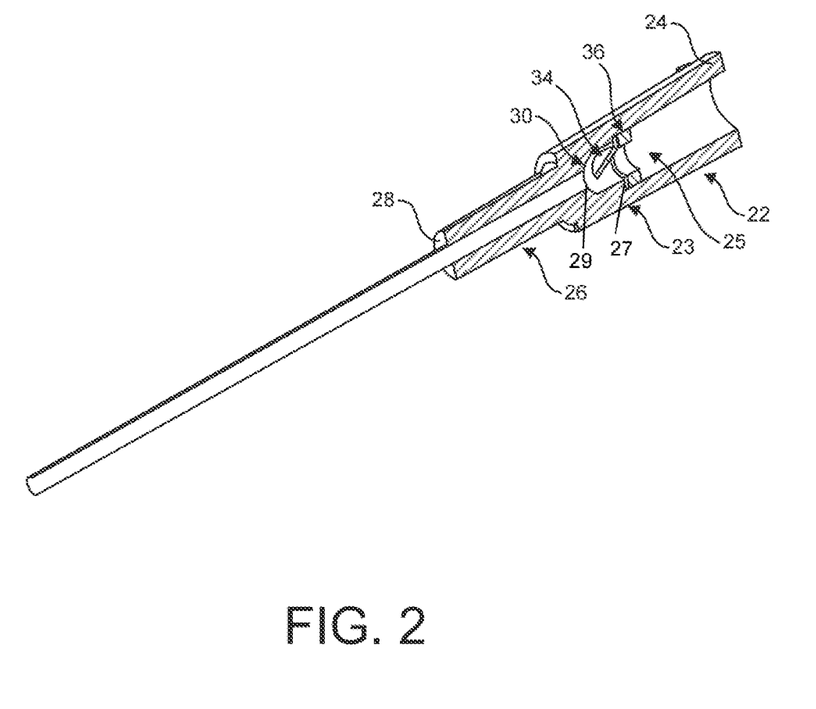
FIG. 2 is a cross-sectional perspective view of the fully assembled connection hub of FIG. 1 with a catheter attached to the connection hub.
Figure 3:
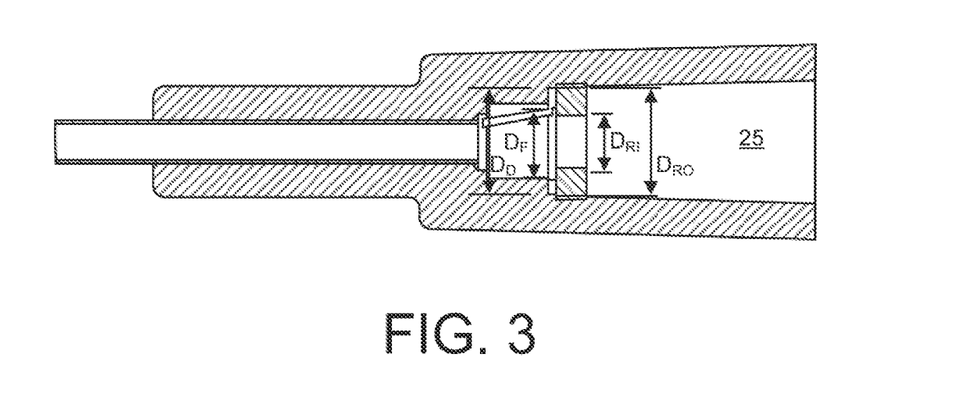
FIG. 3 is a cross-sectional perspective view of the fully assembled connection hub of FIG. 1 with the self-closing valve in the open position.

The connection hub 20 may be any hub that can reversibly connect with a syringe barrel. The connection hub 20 defines at least three sections-a syringe connection section 22 having a receiver end 24 which is adapted to reversibly receive the syringe barrel 60, a catheter connection section 26 having an entry port 29 and a discharge end 28 which connects to the catheter 40, and a transition section 23 located between the syringe connection section 22 and the catheter connection section 26. The transition section 23 must be large enough to allow a valve flap 34 to open into the transition section 23 without obstructing the entry port 29, as shown in FIG. 3.

Exemplary means for reversibly connecting the syringe barrel include, but are not limited to, standard luer-lok fittings or intravenous (IV) tube connection, as are known in the art. The catheter 40 may be fixedly attached to the connection hub 20 or may be reversibly attached using connecting means known in the art, such as standard luer-lok fittings or intravenous (IV) tube connection. In a preferred embodiment, the catheter 40 is fixedly attached to the connection hub 20.

The connection hub 20 can be manufactured from any material which can be produce a semi-rigid device and which can retain the shape of the device during sterilization procedures. Because the practitioner may wish to see blood flowing into and through the connection hub 20, optionally, the connection hub 20 can be manufactured from an essentially translucent material. However, translucency of the material is not required for the connection hub to function as intended.

A bore 25 extends longitudinally through the hub 20 from the receiver end 24 to the entry port 29 and into the discharge end 28. As is known in the art, when the catheter 40 is attached to the discharge end 28, as shown in FIGS. 1-4, the bore 25 is in fluid communication with the catheter 40, and when a syringe barrel is attached to the receiver end 24 the bore 25 allows the syringe barrel to be in fluid communication with the catheter 40. The external configuration and external dimensions of the connection hub 20 do not affect the present invention.

The bore 25 defines a first diameter $D_S$ in the syringe connection section 22, a second diameter Dr in the transition section 23, and a third diameter $D_N$ in the catheter connection section 26. At the point or juncture 27J (not shown) where the syringe connection section 22 meets the transition section 23 the first diameter $D_S$ of bore 25 must be larger than the second diameter $D_T$ of the bore. In a preferred embodiment, the change from the first diameter $D_S$ to the second diameter $D_T$ is sharp so that a shelf 27 is created within the bore 25. At the point where the transition section 23 meets the catheter connection section 26 the second diameter $D_T$ of bore 25 must be larger than the third diameter $D_N$ of the bore, but the narrowing of the bore 25 may be gradual creating a tapered contour. The transition section 23 further defines a length L which is the length from the point where the transition section 23 meets the syringe connection section to the port entry 29.

The self-closing valve 30 is a diaphragm having a slit 32 that transects the diaphragm so that a flap 34 is created that can move when subjected to pressure, such as the movement of fluid through the valve 30. The self-closing valve 30 defines a diaphragm diameter $D_D$ which must be slightly smaller than the bore's syringe section diameter $D_S$ but larger than the bore's transition section diameter $D_T$. Specifically, the diaphragm diameter $D_D$ must be small enough to allow the valve 30 to fit within the bore of the syringe connection section 22 but large enough to fit securely on the shelf 27 to create a barrier between the syringe connection section 22 and the transition section 23. The flap 34 of the valve 30 is created by the slit 32. In a preferred embodiment the slit 32 is an arc with a flap diameter $D_F$ and the flap 34 is created by the slit 32 transecting the diaphragm along at least 50% of the arc. In a more preferred embodiment, the slit 32 transects the diaphragm along at least 80% of the arc. To ensure that the flap 34 does not obstruct the entry port 29, the flap 34 is preferably shorter than the transition section length Lt. In a preferred embodiment, the diaphragm is made of self-sealing elastomeric materials so that the flap 34 "closes" when in a resting state, such as but not limited to silicone, polypropylene, polyurethane, styrenic block copolymers, nitriles, fluoroelastomers, perfluoroelasomers, ethylene propylene, ethylene propylene diene monomers, and combinations thereof.

Figure 4:
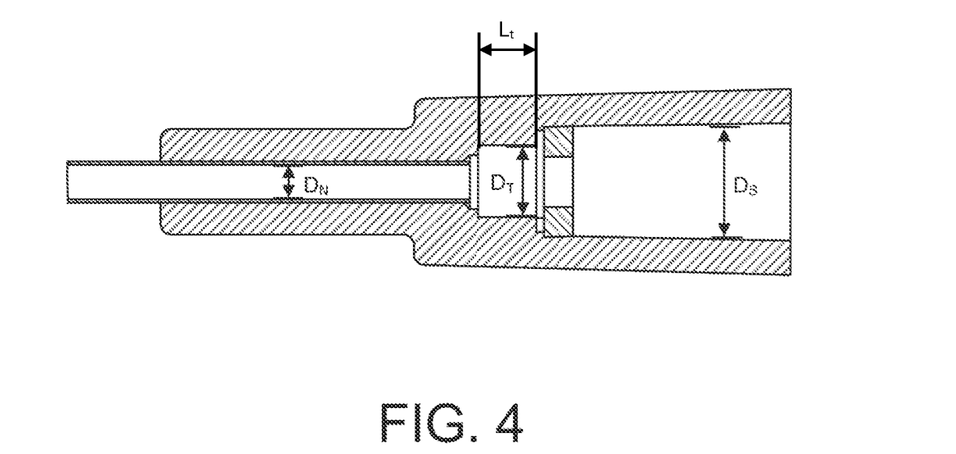
FIG. 4 is a cross-sectional perspective view of the fully assembled connection hub of FIG. 1 with the self-closing valve in the closed position.

The retaining ring 36 is used to hold the self-closing valve 30 tightly against the shelf 27 and to prevent leakage of fluids from the catheter connection section 26 toward the syringe connection section 22. The retaining ring 36 includes an aperture 37 and a body 35 defined by an outer diameter $D_{RO}$ and an inner diameter $D_{RI}$. The outer diameter $D_{RO}$ is essentially equal to the bore's transition section diameter $D_T$ to ensure that the retaining ring 36 can fit within the bore 25 and will remain secured within the bore 25 by friction. The aperture 37 is defined by the retaining ring's inner diameter $D_{RI}$. The inner diameter $D_{RI}$ must be smaller than the valve's flap diameter $D_F$ so that the flap 34 cannot open into the syringe connection section 22. Rather, when the flap 34 experiences backpressure, such as a flow of fluid moving from the catheter connection section 26 toward the syringe connection section 22 as shown in FIG. 4, the flap 34 will be forced against the retaining ring 36 with the slit 32 aligned with the body 35 so any fluid leakage through the slit 32 will be prevented from entering the syringe connection section 22 of the bore 25. In a preferred embodiment, the retaining ring 36 is made of elastomeric materials, such as but not limited to silicone, polypropylene, polyurethane, styrenic block copolymers, nitriles, fluoroelastomers, perfluoroelasomers, ethylene propylene, ethylene propylene diene monomers, and combinations thereof.

The hub assembly 10 of the present invention is prepared by obtaining the connection hub 20 that has the bore 25 and the shelf 27, inserting the self-closing valve 30 into the bore 25 until the valve 30 rests against the shelf 27, and securing the valve 30 against the shelf 27 by inserting the retaining ring 36 into the bore 25. When properly assembled, the retaining ring 36 will remain in position and will hold the valve 30 against the shelf 27 even when the hub assembly 10 is subjected to vibration or jolting.

Except as specifically stated herein, dimensions may vary for all parts of the hub assembly 10. In a first exemplary embodiment, the total length of the hub assembly 10 from the receiver end 24 to the discharge end 28 is about 18.4 mm, the length from the receiver end 24 to the valve 30 is about 5 mm, the inner diameter bore's syringe section diameter $D_S$ is about 6 mm, the diaphragm diameter $D_D$ is about 6 mm, the flap diameter $D_F$ is about 5 mm, the retaining ring outer diameter $D_{RO}$ is about 6 mm, and the retaining ring inner diameter $D_{RI}$ is about 4 mm.

Figure 5:
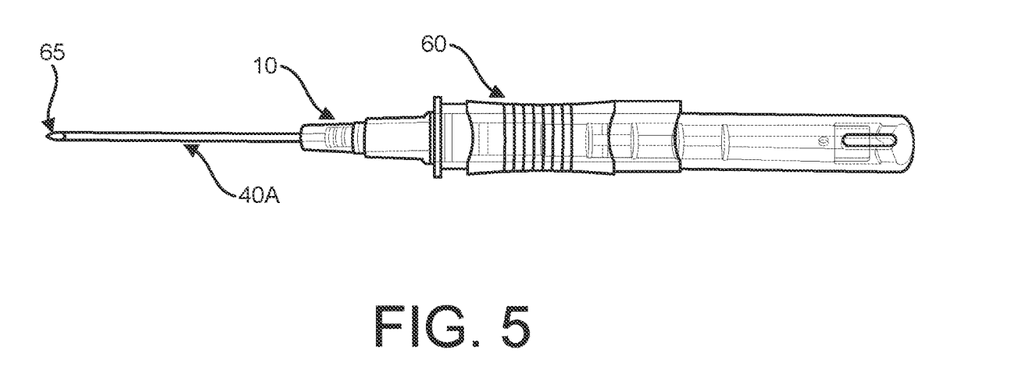
FIG. 5 is a perspective view of the fully assembled connection hub of FIG. 1 fixedly attached to a cannula and provided with a needle and syringe barrel as ready-to-use.
Figure 6:
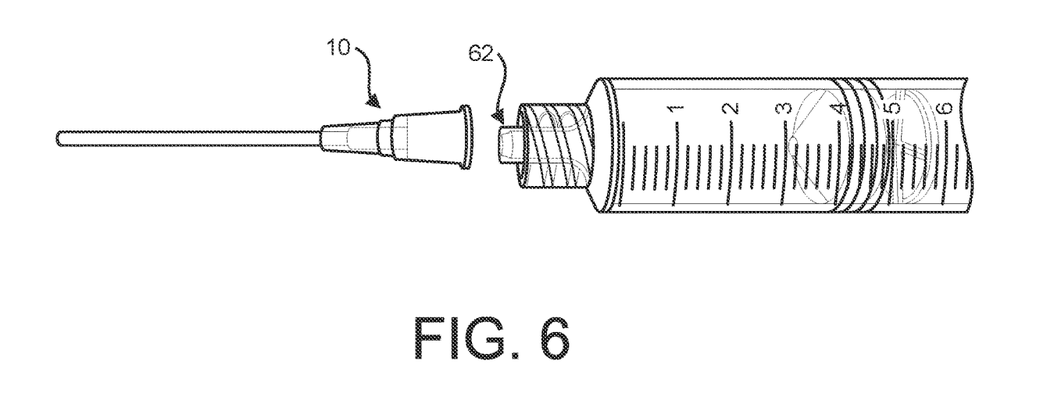
FIG. 6 is a perspective view of the fully assembled connection hub of FIG. 1 fixedly attached to a cannula shown ready to receive the tip of a syringe barrel.

It is anticipated that the hub assembly 10 can be provided to a user in a "ready to use" condition. For example, as shown in FIGS. 5 and 6, the hub assembly 10 with the valve 30 held in position by the retaining ring 36 is fixedly attached to a cannula 40A. A syringe barrel 60 attached to a needle 65 extends through the hub assembly 10 such that the valve flap 34 is held in the open position and the syringe barrel 60 is secured to the receiver end 24 of the hub assembly 10. After the cannula 40A is inserted into a vein, the syringe barrel 60 and needle 65 can be withdrawn from the hub assembly 10 causing the valve flap 34 to close. If blood samples need to be withdrawn or medication needs to be administered, the syringe barrel 60 can be attached to the receiver end 24 of the hub assembly 10 without the needle 65 so that a syringe barrel tip 62 can be project through the valve flap 34 and provide fluid communication to the cannula 40.

Figure 7:
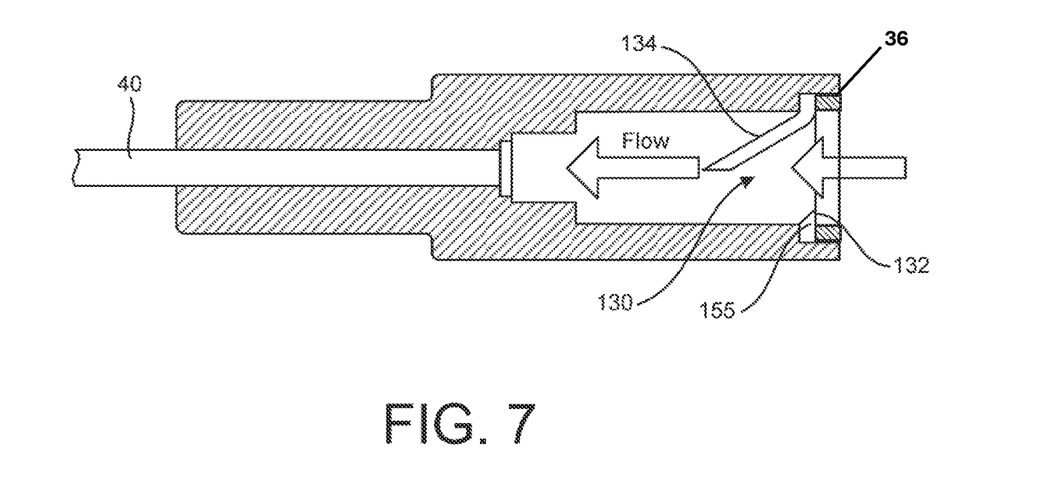
FIG. 7 is a cross-sectional side view of a fully assembled connection hub with a first alternative embodiment self-closing valve positioned to allow for fluid flow into the cannula and showing the valve in the open position.
Figure 8:
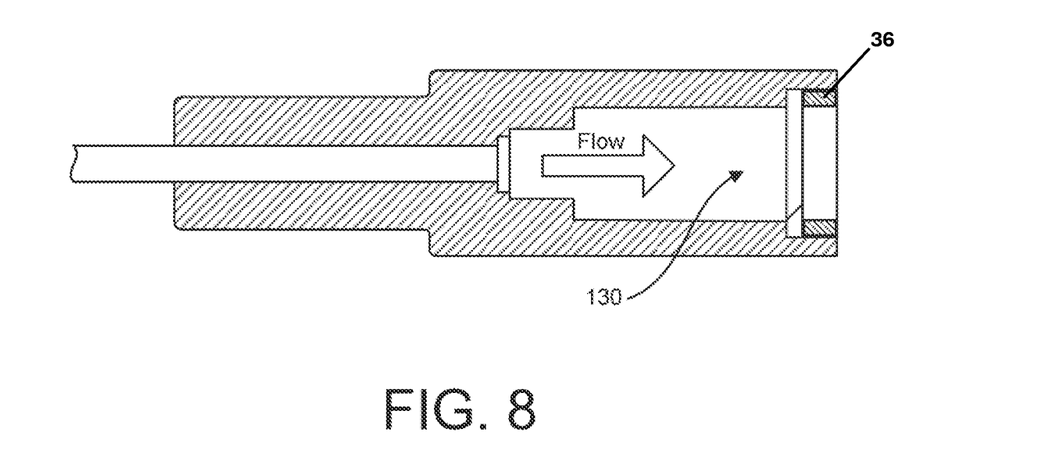
FIG. 8 is a cross-sectional side view of the fully assembled connection hub of FIG. 7 with the self-closing valve in the closed position.
Figure 9:
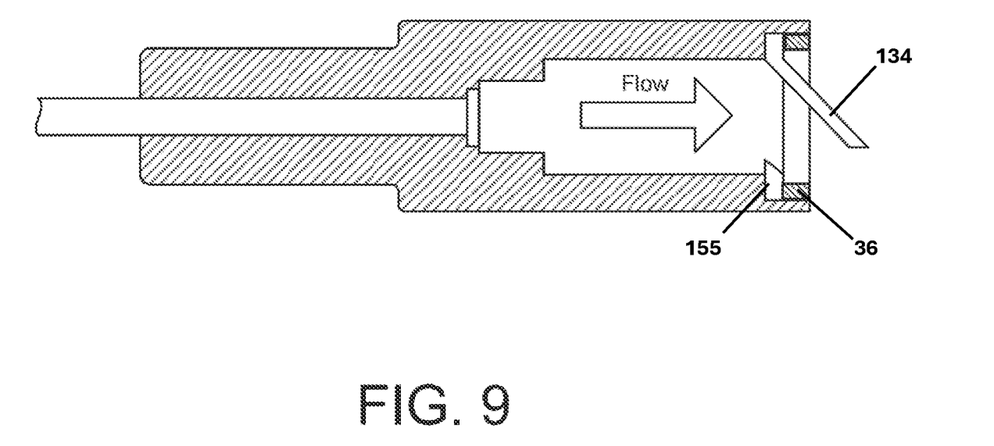
FIG. 9 is a cross-sectional side view of a fully assembled connection hub with the first alternative embodiment self-closing valve positioned to allow for fluid flow from the cannula and showing the valve in the open position; and, FIG. 10 is a cross-sectional side view of the fully assembled connection hub of FIG. 9 with the self-closing valve in the closed position.
Figure 10:
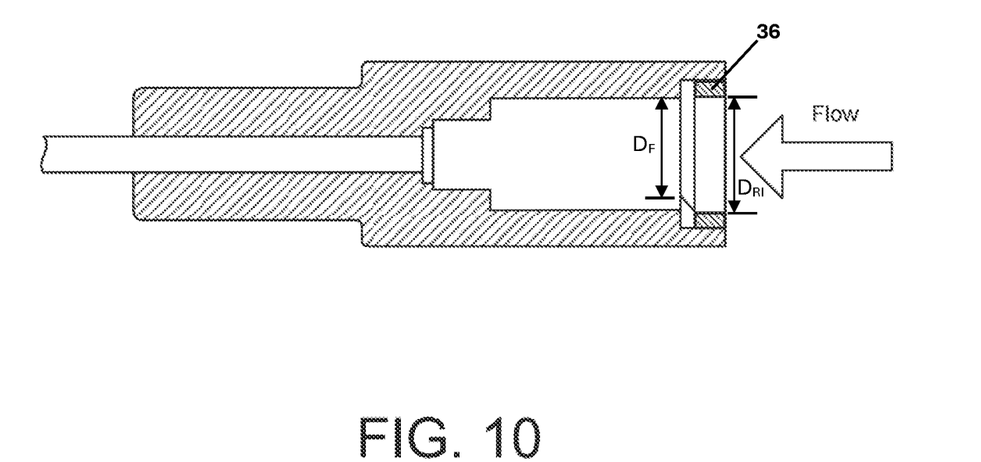

It is anticipated that a first alternative embodiment for the valve 130 may be designed which includes a flap stopper feature, such as shown in FIGS. 7-10. First alternative valve 130 is identical to self-closing valve 30 except valve 130 has a slit 132 cut at approximately a 45° angle relative to the plane of diaphragm to create a beveled flap 134 and a stopper 155. As shown in FIGS. 7 and 9, the valve 130 can be positioned within the syringe connection section 22 to allow fluid to flow through the valve 130 into the cannula 40 or to allow fluid to flow from the cannula 40 through the valve 130. The arrangement as shown in FIG. 9 may be required, for example, to let air and fluids out of a space that has higher pressure than atmospheric pressure, such as when used for chest tubes or urine catheters. As shown in FIGS. 8 and 10, if fluid attempts to flow in a reverse direction than intended, the stopper 155 prevents the flap 134 from opening. In a preferred embodiment, to allow the flap 134 to open into the transition section 23, as shown in FIG. 7, or to open outward from the transition section 23, as shown in FIG. 9, the flap diameter $D_F$ is preferably smaller than the inner diameter $D_{RI}$ of the aperture of the retaining ring.

Unless defined otherwise, all technical and scientific terms used herein have the same meaning as commonly understood by one of ordinary skill in the art to which the presently disclosed subject matter pertains. Representative methods, devices, and materials are described herein, but are not intended to be limiting unless so noted.

The terms "a", "an", and "the" refer to "one or more" when used in the subject specification, including the claims.

Unless otherwise indicated, all numbers expressing quantities of components, conditions, and otherwise used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to a measurement or a dimension can encompass variations of, in some embodiments±20%, in some embodiments±10%, in some embodiments±5%, in some embodiments±1%, in some embodiments±0.5%, and in some embodiments to ±0.1%, from the specified value, as such variations are appropriate in the disclosed application.

It is understood that, in light of a reading of the foregoing description, those with ordinary skill in the art will be able to make changes and modifications to the present invention without departing from the spirit or scope of the invention, as defined herein. For example, those skilled in the art may substitute materials supplied by different manufacturers than specified herein without altering the scope of the present invention.

What is claimed is:

1. A hub assembly comprising:
   a. a connection hub, wherein the connection hub defines a syringe connection section having a receiver end and a catheter connection section having a discharge end, and wherein a bore extends longitudinally through the hub from the receiver end to the discharge end;
   b. a self-closing valve having a flap created by a slit in a diaphragm, wherein the flap of the self-closing valve is formed by transecting the diaphragm with an arc and at an angle to create a beveled flap and a complementary beveled stopper; and,
   c. a retaining ring having an aperture, wherein the retaining ring is sized and positioned to secure the self-closing valve in the bore of the connection hub;
   wherein the self-closing valve is positioned in the bore of the connection hub between the receiver end and the discharge end such that the flap can be moved from a closed position to an open position, and wherein the retaining ring is positioned in the bore between the self-closing valve and the receiver end with the retaining ring abutting the self-closing valve, and holding the self-closing valve in the bore of the connection hub by friction.

2. The hub assembly of claim 1 wherein the aperture of the retaining ring defines an inner diameter $D_{RI}$, the valve flap defines a diameter $D_F$, and the inner diameter $D_{RI}$ is smaller than the flap diameter $D_F$.

3. The hub assembly of claim 1 wherein the angle is approximately a 45° angle relative to a plane of the diaphragm so that the flap and the stopper are beveled.

4. The hub assembly of claim 1 wherein the aperture of the retaining ring defines an inner diameter $D_{RI}$, and the valve flap defines a diameter $D_T$, and the flap diameter $D_F$ is smaller than the inner diameter $D_{RI}$.

5. A hub assembly comprising:
   a. a connection hub, wherein the connection hub defines a syringe connection section having a receiver end, a catheter connection section having a discharge end and an entry port, and a transition section located between the syringe connection section and the catheter connection section, and wherein a bore extends longitudinally through the hub from the receiver end to the discharge end, and wherein the bore defines a first diameter $D_S$ in the syringe connection section, a second diameter $D_T$ in the transition section, and a third diameter $D_N$ in the catheter connection section, and $D_S$ is larger than $D_T$ and $D_T$ is larger than $D_N$, and a shelf is created within the bore at a juncture of the syringe connection section and the transition section;
   b. a self-closing valve having a flap created by a slit in a diaphragm, wherein the slit is an arc with a flap diameter $D_F$, and wherein the flap is formed by transecting the diaphragm at an angle to create a stopper; and,
   c. a retaining ring having an aperture, wherein the retaining ring is sized and positioned to secure the self-closing valve in the connection hub;
   wherein the self-closing valve is positioned between the shelf and the retaining ring, and the retaining ring holds the self-closing valve in the bore of the connection hub by friction.

6. The hub assembly of claim 5 further comprising a needle, a catheter, or a cannula fixedly secured to the discharge end of the connection hub.

7. The hub assembly of claim 5 wherein the receiver end is adapted to reversibly receive a syringe barrel.

8. The hub assembly of claim 7 wherein the receiver end is adapted with a luer-lok fitting or an intravenous tube connection.

9. A hub assembly comprising:
   a. a connection hub, wherein the connection hub defines a syringe connection section having a receiver end and a catheter connection section having a discharge end, and wherein a bore extends longitudinally through the connection hub from the receiver end to the discharge end;
   b. a self-closing valve having a flap and a stopper, wherein the flap and the stopper are created by a slit in a diaphragm that allows the flap to open in response to a fluid flowing in a forward direction, and causes the flap to abut the stopper and be prevented from opening in response to a fluid flow in a reverse direction;
   c. a retaining ring having an aperture, wherein the retaining ring is sized and positioned to secure the self-closing valve in the bore of the connection hub;

wherein the self-closing valve is positioned in the bore of the connection hub between the receiver end and the discharge end such that the flap can be moved from a closed position to an open position, and the retaining ring is positioned in the bore between the self-closing valve and the receiver end, with the retaining ring abutting the self-closing valve and holding the self-closing valve in the bore of the connection hub by friction.

10. The hub assembly of claim 9 wherein the slit is made at an angle approximately 45° relative to a plane of the diaphragm so that the flap and the stopper are beveled.

11. The hub assembly of claim 9 wherein the aperture of the retaining ring defines an inner diameter $D_{RI}$, the flap defines a diameter $D_F$, and the flap diameter $D_F$ is smaller than the inner diameter $D_{RI}$.

12. The hub assembly of claim 9 wherein the aperture of the retaining ring defines an inner diameter $D_{RI}$, the flap defines a diameter $D_F$, and the flap diameter $D_F$ is larger than the inner diameter $D_{RI}$.

* * * * *